(12) United States Patent
Tanner

(10) Patent No.: US 6,544,253 B1
(45) Date of Patent: Apr. 8, 2003

(54) SURGICAL SUPPORT DEVICE AND METHOD OF USING THE SAME

(75) Inventor: Howard Tanner, Logan, UT (US)

(73) Assignee: Eva Corporation, Bethesda, MD (US)

( * ) Notice: Subject to any disclaimer, the term of this patent is extended or adjusted under 35 U.S.C. 154(b) by 0 days.

(21) Appl. No.: 09/121,705

(22) Filed: Jul. 24, 1998

(51) Int. Cl.[7] .................................................. A61F 2/06
(52) U.S. Cl. ........................ 606/1.23; 606/198; 606/159
(58) Field of Search .......................... 606/1, 108, 191, 606/192, 194, 198, 184, 185, 190, 159, 170, 171; 623/1, 12, 1.1, 1.11, 1.23; 604/96

(56) References Cited

U.S. PATENT DOCUMENTS

| | | | |
|---|---|---|---|
| 4,562,596 A | | 1/1986 | Kornberg |
| 4,787,899 A | | 11/1988 | Lazarus |
| 5,042,707 A | | 8/1991 | Taheri |
| 5,242,451 A | * | 9/1993 | Harada et al. ............... 606/198 |
| 5,292,321 A | * | 3/1994 | Lee ............................ 606/198 |
| 5,443,477 A | * | 8/1995 | Marin et al. ................ 606/198 |
| 5,507,768 A | * | 4/1996 | Lau et al. .................... 623/1.1 |
| 5,676,696 A | | 10/1997 | Marcade |
| 5,759,150 A | * | 6/1998 | Konou et al. ................ 606/190 |
| 5,785,679 A | * | 7/1998 | Abolfathi et al. ........... 606/194 |
| 5,871,537 A | * | 2/1999 | Holman et al. .............. 606/194 |
| 5,876,367 A | * | 3/1999 | Kaganov et al. ............ 606/200 |
| 6,059,802 A | * | 5/2000 | Ginn .......................... 606/159 |

\* cited by examiner

Primary Examiner—Michael J. Milano
Assistant Examiner—(Jackie) Tan-Uyen T. Ho
(74) Attorney, Agent, or Firm—John N. Coulby; Collier Shannon Scott, PLLC

(57) ABSTRACT

The surgical support device is disclosed for use during a surgical procedure. The surgical support device includes a support assembly for supporting a surgical component during the surgical procedure. A stabilizing assembly stabilizes the support device within a vessel during the surgical procedure. The support device further includes a manipulating assembly for adjusting the position of the surgical component. The surgical support device may also be beneficially used as a 'partial' or 'controlled' occlusion balloon having the benefit of facilitating intermittent or lower level profusion to the extremities during a surgical procedure.

21 Claims, 3 Drawing Sheets

US 6,544,253 B1

SURGICAL SUPPORT DEVICE AND METHOD OF USING THE SAME

FIELD OF THE INVENTION

The present invention relates generally to a surgical support device for use in vascular surgical procedures. In particular, the present invention relates to an inflatable surgical support device.

BACKGROUND OF THE INVENTION

The inventor of the subject matter of the present invention is aware of no prior attempts to support a graft within a vessel during a surgical procedure using a selectively inflatable support device.

OBJECTS OF THE INVENTION

It is therefore an object of the present invention to provide a support device for a graft assembly.

It is another object of the present invention to provide a surgical support device that aids in the location of graft components during a surgical procedure.

It is another object of the present invention to provide a surgical support device that is capable of supporting a graft during a surgical procedure.

It is another object of the present invention to provide a surgical support device that is capable of supporting a graft during a surgical procedure to prevent damaging off-axis placement of the graft during a surgical procedure.

It is another object of the present invention to provide a surgical support device that can be used as an occlusion balloon which permits intermittent blood flood to the extremities during a surgical procedure.

SUMMARY OF THE INVENTION

The present invention is directed to a support device for use in a surgical procedure. The support device is capable of supporting a graft assembly within a vessel. The present invention, however, is not limited to the support of a graft assembly within a vessel; rather, it is contemplated by the inventor of the present invention that the support device may support numerous surgical components during various surgical procedures. The support device according to the present invention includes a support assembly for supporting a surgical component during a surgical procedure. The support device also includes a stabilizing assembly for stabilizing the support device within a vessel during the surgical procedure.

According to the present invention, the stabilizing assembly may be secured to the support assembly. The support assembly includes an assembly for receiving a surgical component. The assembly for receiving a surgical device may include a hollow assembly for receiving the surgical device therein. The hollow assembly may include a central passageway for receiving the surgical device therethrough.

The stabilizing assembly may include an expandable assembly for engaging the vessel to stabilize the support device within the vessel. The expandable assembly may include at least one expandable chamber. The at least one expandable chamber may be inflatable. The support assembly may include an assembly for inflating the at least one expansible chamber. The expansible assembly may be secured to the support assembly.

The support device may further include a manipulating assembly for manipulating a graft assembly within the vessel during the surgical procedure. The manipulating assembly may include at least one position adjusting assembly for adjusting the position of the graft support within the vessel. The at least one position adjusting assembly may extend through at least one passageway in the support device. The at least one passageway may be located on the supporting assembly. Alternatively, the at least one passageway may be located on the stabilizing assembly. Additionally, the supporting assembly may act as a fulcrum for the at least one position adjusting assembly to adjust the position of the graft assembly within the vessel. Each of the at least one position adjusting assembly may comprise a control line.

The present invention is also directed to a method of supporting a graft assembly within a vessel during a surgical procedure. The method includes the steps of positioning the graft assembly within the vessel, and supporting the graft assembly within the vessel using a support device. The step of supporting the graft assembly may include the step of expanding an expandable assembly on the support device to securely locate the graft assembly within the vessel. The method may further include the step of adjusting the position of the graft assembly within the vessel by manipulating the support device.

It is to be understood that both the foregoing general description and the following detailed description are exemplary and explanatory only, and are not restrictive of the invention, as claimed. The accompanying drawings, which are incorporated herein by reference, and which constitute a part of this specification, illustrate certain embodiments of the invention, and together with the detailed description serve to explain the principles of the present invention.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1:
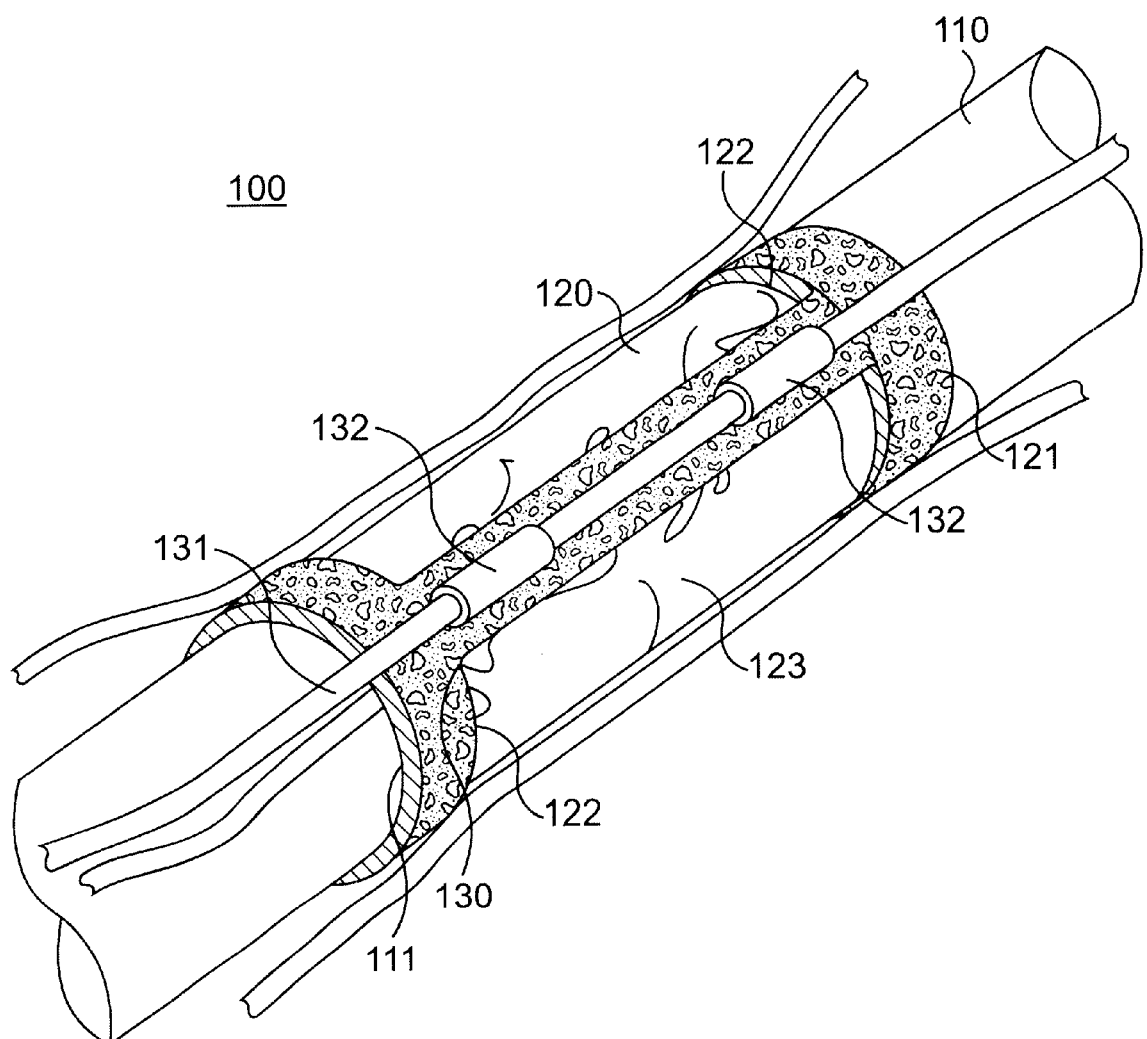
FIG. 1 is a perspective view of a graft support assembly in a collapsed position according to an embodiment of the present invention.

The present invention will now be described in connection with the surgical repair of an abdominal aortic aneurysm. The invention, however, is not limited solely to use in the repair of the abdominal aortic aneurysms; rather, it is contemplated that the surgical support device according to the present invention may be used in other vascular surgeries.

An embodiment of the surgical support device 100 will now be described in connection with FIGS. 1–3. The surgical support device 100 includes a support assembly 110. The support assembly 110 is preferably a catheter. The catheter 110 is preferably formed from a polymeric material, such as KYNAR, and PEBAX. The catheter 110 includes at least one passageway. The catheter 110 preferably includes a central passageway 111, as shown in FIG. 3. The central passageway 111 is sized to receive guide wires or a procedure specific device such as the penetration assembly and the visualization assembly disclosed in U.S. patent application Ser. No. 08/896,415, now U.S. Pat. No. 5,544,750 entitled "METHOD AND APPARATUS FOR THE SURGICAL REPAIR OF ANEURYSMS", the disclosure of which is incorporated herein by reference. The catheter 110 preferably includes at least one smaller lumen 112 within the catheter wall. The smaller lumen permit the passage of an inflation gas or fluid to the stabilizing assembly 120, described below.

A stabilizing assembly 120 is provided on the catheter 110 to support the support device 100 within a vessel during the surgical procedure. The stabilizing assembly 120 includes a sleeve 121 located at one end of the catheter 110. The sleeve 121 includes at least one opening 122 therein, as shown in FIGS. 1 and 2. An expandable assembly 123 is located within each of the at least one opening 122. The expandable assembly 123 forms an expansible chamber. The expansible chamber is fluidically connected to one of the at least one smaller lumen 112 such that fluid or gas may be introduced into the chamber to expand the expandable assembly, as shown in FIG. 2.

Figures 2, 3:
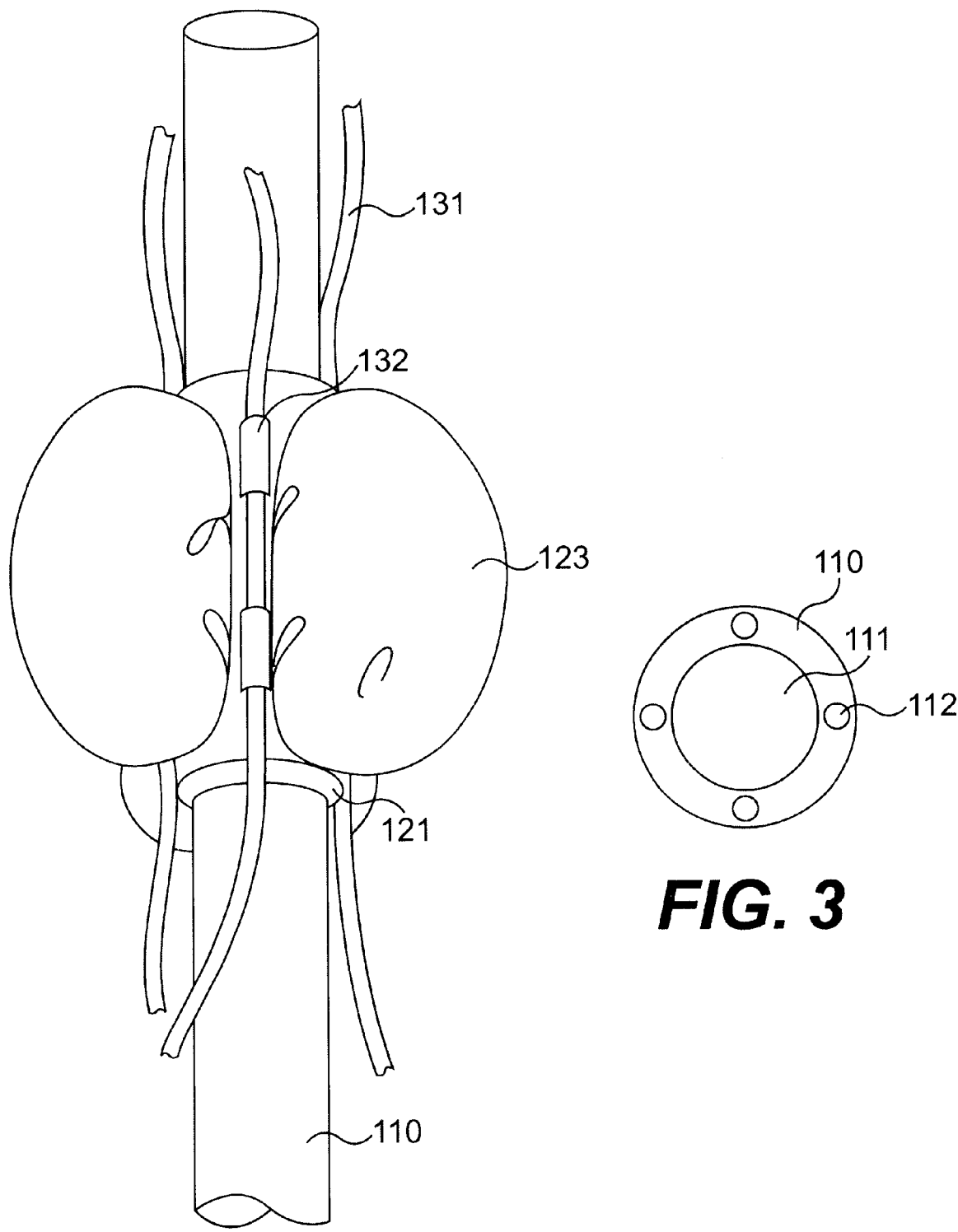
FIG. 2 is a perspective view of the graft support assembly of FIG. 1 in an inflated configuration.
FIG. 3 is a side view of the shaft of the surgical support assembly of FIG. 1.

As shown in FIGS. 1 and 2, the stabilizing assembly 120 contains more than one expansible assembly 123. Each expansible assembly 123 may be interconnected with adjacent expansible assemblies such that each may be expanded through the passage of fluid or gas through a single smaller lumen 112. It, however, is contemplated that separate smaller lumen 112 may be used to expand each expansible assembly 123.

At least one manipulating assembly 130 is located on the periphery of the sleeve 121, as shown in FIGS. 1 and 2. The manipulating assembly 130 is provided to permit manoeuvering and adjustment of a surgical component, such as a repair graft that is located within the vessel. Each manipulating assembly 130 includes a guide wire 131 and an at least one attachment assembly 132 for slidably securing the guide wire 131 to the collar 121. The at least one attachment assembly 132 is located between adjacent openings 122 in the sleeve 121. Each guide wire 131 may be secured to for example the repair graft. Manipulating the guide wires 131 will permit the manipulation of the repair graft within the vessel to insure proper alignment during the repair procedure.

Another embodiment of the surgical support device 200 will now be described in connection with FIG. 4. The surgical support device 200 includes a support assembly 110. As described above, the support assembly 110 is preferably a catheter that is formed from a polymeric material. The catheter 110 contains at least one passageway, as discussed for example in connection with FIG. 2.

The surgical support device 200 includes a stabilizing assembly 220. The stabilizing assembly 220 is located on one end of support device 200. The stabilizing assembly 220 includes two collars 221. An expandable assembly 223 incorporates collars 221. The expandable assembly 223 includes an expansible chamber. The expansible chamber is fluidically connected to smaller lumen within the support assembly 110 such that fluid or gas may be introduced into the expansible chamber to expand the expansible assembly, as shown in FIG. 4.

Figure 4:
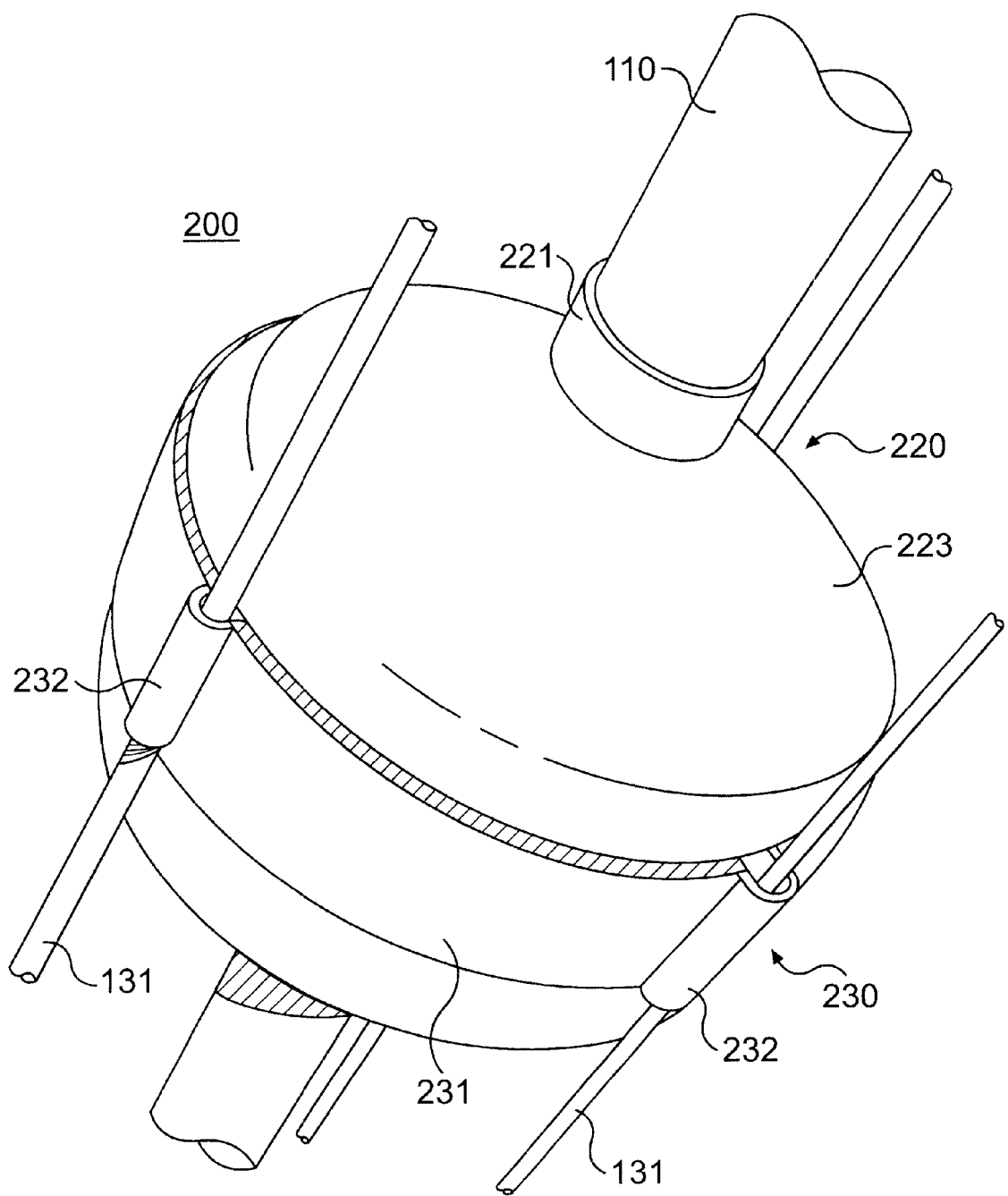
FIG. 4 is a perspective view of another embodiment of the present invention in an inflated position.

The embodiment illustrated in FIG. 4 contains a single expansible assembly 223. A manipulating assembly 230 is located on the periphery of the expansible assembly 223. The manipulating assembly 230 includes a flexible collar 231, at least one attachment assembly 232 and at least one guide line 131. Manipulation of the guide lines 131 will permit the manipulation of the repair graft within the vessel to insure proper on axis alignment during the repair procedure.

The operation of the surgical support device 100 will now be described in connection with the repair of a abdominal aortic aneurysm. A guide wire is fed from a femoral incision to a left axillary incision. The guide lines 131 that are attached to the repair graft lip are then attached to the guide wire at the femoral incision. The guide wire is withdrawn at the axillary incision until the guide lines are accessible and the repair graft assumes an infra, juxta, suprarenal positioning. The guide lines are then fed through the attachment assemblies 132 of the sleeve 121 and the surgical support device 100 is then fed over the guide lines 131 until it assumes an appropriate positioning with respect to the repair graft.

Fluid such as saline solution or a suitable gas is fed through the smaller lumen 112 to expand the at least one expansible assembly 123. Once expanded, the at least one expansible assembly 123 maintains the support device 100 in a fixed position within the vessel. The penetration assembly or visualization assembly described above may then be inserted to secure the repair graft to the vessel. The position of the repair graft may then be adjusted by manipulating guide lines 131. Once the repair graft has been secured to the vessel wall, the fluid can be removed such that the at least one expansible assembly 123 collapses to permit removal of the support device 100. The guide lines 131 will remain in the vessel after the removal of the support device. A suitable cutting device may then be introduced into the vessel to remove the guide wires 131.

The surgical support device 200 is operated in a similar manner.

Specifically, the surgical support device 100 may also be beneficially used as a "partial" or "controlled" occlusion balloon having the benefit of facilitating intermittent or lower level blood flow or profusion to the extremities (caudad) during a surgical procedure. This may be accomplished by releasing pressure within the at least one expandible assembly 123. This creates openings between adjacent expandible assemblies to permit the flow of blood. The expandible assemblies are still sufficiently expanded such that the support device 100 maintains its position within the vessel.

It will be apparent to those skilled in the arts that various modifications and variations can be made in the construction and configuration of the present invention, without departing from the scope or spirit of the invention. It is intended that the present invention cover the modifications and variations of the invention, provided they come within the scope of the appended claims and their equivalence.

What is claimed is:

1. A support device for use in supporting and manipulating a surgical component during a surgical procedure, said support device comprising:

support means for supporting the surgical component during the surgical procedure;

stabilizing means for stabilizing said support device within a vessel during the surgical procedure; and manipulating means for manipulating the surgical component within the vessel during the surgical procedure, wherein said manipulating means includes at least one position adjusting assembly for adjusting the position of the surgical component within the vessel, wherein said at least one position adjusting assembly is located on the exterior of said support means.

2. The support device according to claim 1, wherein said stabilizing means is secured to said support means.

3. The support device according to claim 1, wherein said support means includes means for receiving the surgical component.

4. The support device according to claim 1, wherein said stabilizing means includes an expandable assembly for engaging the vessel to stabilize said support device within the vessel.

5. The support device according to claim 4, wherein said expandable assembly includes at least one expandable chamber.

6. The support device according to claim 5, wherein said support means includes means for receiving the surgical component.

7. The support device according to claim 6, wherein said support means includes means for inflating said at least one expandable chamber.

8. The support device according to claim 4, wherein said expandable assembly is secured to said support means.

9. The support device according to claim 1, wherein said at least one position adjusting assembly extends through at least on passageway located on said support means.

10. A method of supporting a graft assembly within a vessel during a surgical procedure, said method comprising the steps of:
   securing the graft assembly to a support device, wherein said support device comprises a support means for supporting said graft assembly during said surgical procedure wherein said support device further comprises a stabilizing means for stabilizing said support device within a vessel during said surgical procedure, wherein said support device still further comprises a manipulating means secured to the graft assembly for manipulating said graft assembly within the vessel during said surgical procedure, wherein said manipulating means includes at least one position adjusting assembly for adjusting the position of the graft support within the vessel, wherein said at least one position adjusting assembly is located on the exterior of said support means;
   inserting the graft assembly and the support device in the vessel;
   positioning the graft assembly and the support device at a desired location within the vessel; and
   supporting the graft assembly within the vessel using the support device.

11. The method according to claim 10, further comprising the step of adjusting the position of the graft assembly within the vessel by manipulating the support device.

12. The method according to claim 10, wherein said step of supporting the graft assembly includes the step of expanding an expandable assembly on the support device to securely locate the graft assembly within the vessel.

13. The method according to claim 10, wherein the support device includes at least one control line, wherein said step of securing the graft assembly to the support device includes the step of securing the at least one control line to the graft assembly.

14. The method according to claim 13, further comprising the step of adjusting the position of the graft assembly within the vessel by manipulating the support device.

15. The method according to claim 14, wherein said step of adjusting the position of the graft assembly within the vessel includes the step of manipulating the at least one control line to adjust the position of the graft assembly.

16. A support device for use in a surgical procedure, said support device comprising:
   support means for supporting a graft assembly during a surgical procedure;
   stabilizing means for stabilizing said support device within a vessel during the surgical procedure; and
   manipulating means secured to the graft assembly for manipulating the graft assembly within the vessel during the surgical procedure, wherein said manipulating means includes at least one position adjusting assembly for adjusting the position of the graft support within the vessel, wherein said at least one position adjusting assembly is located on the exterior of said support means.

17. The support device according to claim 16, wherein said at least one position adjusting assembly extends through at least one passageway on said support device.

18. The support device according to claim 17, wherein said at least one passageway is located on said support means.

19. The support device according to claim 16, wherein said at least one passageway is located on said stabilizing means.

20. The support device according to claim 16, wherein said at least one position adjusting assembly is a control line.

21. The support device according to claim 16, wherein said support means includes an expandable assembly for securely locating the graft assembly within the vessel.

* * * * *